(12) United States Patent
Yarbrough et al.

(10) Patent No.: US 7,655,826 B2
(45) Date of Patent: Feb. 2, 2010

(54) METHOD FOR DECOMPOSITION OF ETHERS

(75) Inventors: Charles M. Yarbrough, Baton Rouge, LA (US); Vijay Swarup, Prairieville, LA (US); Patrick Joseph Maher, Kingwood, TX (US); Albert Y Hu, Baton Rouge, LA (US); Michael Walter Bedell, Baton Rouge, LA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 704 days.

(21) Appl. No.: 11/104,315

(22) Filed: Apr. 12, 2005

(65) Prior Publication Data

US 2006/0229481 A1 Oct. 12, 2006

(51) Int. Cl.
*C07C 4/02* (2006.01)
*C07C 1/00* (2006.01)
*C10G 9/00* (2006.01)
*C10G 11/00* (2006.01)

(52) U.S. Cl. ........................ 585/653; 585/638; 585/639; 585/640; 585/648; 585/651; 208/67; 208/106; 208/113; 208/121; 208/130

(58) Field of Classification Search .................. 585/648, 585/651, 652, 653, 638–640; 208/106.67, 208/113, 121, 130
See application file for complete search history.

(56) References Cited

U.S. PATENT DOCUMENTS

| 3,966,586 | A | * | 6/1976 | Owen et al. | ............ 208/120.01 |
| 4,254,296 | A | | 3/1981 | Manara et al. | .............. 585/640 |
| 4,352,945 | A | | 10/1982 | Bezman | ...................... 568/899 |
| 4,592,826 | A | * | 6/1986 | Ganguli | ....................... 208/407 |
| 4,788,377 | A | * | 11/1988 | Chang et al. | ................. 585/640 |
| 5,171,920 | A | | 12/1992 | Chaumette et al. | .......... 585/640 |
| 5,914,433 | A | | 6/1999 | Marker | ........................ 585/313 |
| 6,100,438 | A | * | 8/2000 | Marion et al. | ................ 585/639 |
| 7,067,053 | B2 | * | 6/2006 | Cotte et al. | .................. 208/431 |

FOREIGN PATENT DOCUMENTS

EP 0 123 449 10/1983

* cited by examiner

*Primary Examiner*—In Suk Bullock
(74) *Attorney, Agent, or Firm*—Andrew B. Griffis

(57) ABSTRACT

This invention relates to a method of making an olefin from a dialkyl ether comprising (a) introducing an ether having a formula $C_xH_{2x+1}C_yH_{2y+1}$ into a thermal or catalytic cracking unit processing a hydrocarbon feedstock; and (b) decomposing at least a portion of the ether to form an olefin having a formula $C_xH_{2x}$ and/or $C_yH_{2y}$ and an alcohol having a formula $C_xH_{2x+1}$ and/or $C_yH_{2y+1}OH$, wherein x and y independently range from about 1 to about 30. This invention also relates to a method of reducing coking in a thermal or catalytic cracking unit comprising (a) introducing an ether, having a formula $C_xH_{2x+1}OC_yH_{2y+1}$, into the cracking unit processing a hydrocarbon feedstock in an amount effective to reduce coke formation relative to processing the hydrocarbon feedstock in the absence of the ether, wherein x and y independently range from about 1 to about 30.

6 Claims, 2 Drawing Sheets

METHOD FOR DECOMPOSITION OF ETHERS

FIELD OF THE INVENTION

This invention relates to the decomposition of dialkyl ethers. More particularly, the invention relates to a method of decomposition of dialkyl ethers in catalytic or thermal cracking units. The invention also related to a method of reducing coking in hydrocarbon thermal or catalytic cracking units.

BACKGROUND OF THE INVENTION

Ethers are manufactured in many processes either directly or as side products to the production of other oxygenates. Examples include isopropyl ether (IPE) from the production of isopropyl alcohol (IPA), secondary butyl ether (SBE) from the production of methyl ethyl ketone (MEK), methyl tertiary butyl ether (MTBE) from MTBE production units or isobutylene purification, tertiary amyl ether (TAME) from amylene production, $C_8$ to $C_{30}$ ethers from the production of oxo alcohols as well as many others.

Currently, many of the small ethers having $C_4$ to $C_{10}$ carbon chain length are blended into motor gasoline (Mogas) for oxygenate content. Legislation is progressing that may prevent this disposition from being available. This necessitates finding alternate dispositions for these ethers.

U.S. Pat. No. 4,254,296 discloses a process for the preparation of tertiary olefins starting from the corresponding alkyl tert-alkyl ethers, characterized in that the tert-alkyl ethers are reacted in the presence of a catalyst selected from the group consisting of a crystalline silica having a high specific surface area corresponding to the general formula $0\text{-}1M_nO_m \cdot 1SiO_2$, wherein $M_nO_m$ is the oxide of a metallic cation capable of entering into the silica lattice as a substituent for silicon or as a salt of polysilicic acids and/or an aluminum-modified silica corresponding to the general formula as follows: $0.0006\text{-}0.0025\ Al_2O_3 \cdot 1SiO_2$.

U.S. Pat. No. 4,395,580 discloses a process for producing a tertiary olefin of the formula: $R_2CH=CR_1R_3$ by decomposition of the corresponding tertiary ether of the formula: $R_2CH_2C(R_1)(R_3)\text{—}O\text{—}CH_2R$ wherein $R_1$ and $R_3$ are each independently an alkyl, arylalkyl, aryl or alkylaryl radical; and $R_2$ and R are each independently a hydrogen atom or an alkyl, arylalkyl, aryl or alkylaryl radical, said process comprising the step of contacting said ether, in the presence of steam, the molar ratio $H_2O$ tertiary ether being from 2 to 8, with a catalyst consisting essentially of alumina having deposited thereon at least one modifying agent, said agent being titanium, zirconium or hafnium, as the elemental metal or a metal compound, the content of said metal or metal compound, expressed as the elemental metal, being 0.01-5% by weight with respect to the alumina, said alumina, after incorporation of the metal or metal compound, having a specific surface of 80-300 $m^2/g$; whereby the tertiary olefin is produced in high purity, and parasitic side-reactions which decrease the yields of tertiary olefin and of recovered alcohol are minimized.

U.S. Pat. No. 5,914,433 discloses a process for producing polymer grade olefins comprising a) passing an oxygenate feedstock comprising an alcohol or an ether having from 1 to 4 carbon atoms per molecule to a fluidized reaction zone containing an aluminophosphate molecular sieve catalyst in the presence of a diluent at conditions effective to convert the oxygenate feedstock to a light olefin product stream comprising ethylene, propylene, and butylene and to produce a spent aluminophosphate molecular sieve catalyst; b) passing the light olefin product stream to a separation zone to separate the light olefin product stream into an ethylene stream, a propylene stream, and a mixed butylene and heavier stream; c) withdrawing at least a portion of the spent aluminophosphate molecular sieve catalyst from the fluidized reaction zone and passing the spent aluminophosphate molecular sieve catalyst to a regenerator to regenerate the spent aluminophosphate molecular sieve catalyst with an oxygen-containing stream to produce a regenerated catalyst; and d) returning a first portion of the regenerated catalyst to the fluidized reaction zone and admixing a second portion of the regenerated catalyst with a portion of the mixed butylene and heavier stream to provide a feed admixture and passing the feed admixture to a cracking reaction zone at conditions effective to convert the mixed butylene and heavier stream to produce a second product stream comprising additional amounts of ethylene and propylene and to produce a third regenerated catalyst portion; and e) passing at least a portion of the second product stream to the fluidized reaction zone.

Additional references of interest include: U.S. Pat. Nos. 4,352,945; 5,171,920; 5,227,564; and EP 0 123 449 A1.

SUMMARY OF THE INVENTION

In a one embodiment, this invention relates to a method of making an olefin from a dialkyl ether comprising (a) introducing at least about 1000 ppm by weight of an ether having a formula $C_xH_{2x+1}OC_xH_{2x+1}$ into a thermal or catalytic cracking unit processing a hydrocarbon feedstock; and (b) decomposing at least a portion of the ether to form an olefin having a formula $C_xH_{2x}$ and/or an alcohol having a formula $C_xH_{2x+1}OH$, wherein x ranges from about 1 to about 30.

In another embodiment, this invention relates to a method of making an olefin from a dialkyl ether comprising (a) introducing at least about 1000 ppm by weight of one ether having a formula $C_xH_{2x+1}OC_yH_{2y+1}$ into a thermal or catalytic cracking unit processing a hydrocarbon feedstock; and (b) decomposing at least a portion of the ether to form (1) an olefin having a formula $C_xH_{2x}$ and an alcohol having a formula $C_yH_{2y+1}OH$ and/or (2) an olefin having a formula $C_yH_{2y}$ and an alcohol having a formula $C_xH_{2x+1}OH$, wherein x and y independently range from about 1 to about 30.

In another embodiment, this invention relates to a method of making an olefin from a dialkyl ether comprising (a) introducing a hydrocarbon feedstock into a thermal or catalytic cracking unit; (b) injecting at least one ether having a formula $C_xH_{2x+1}OC_yH_{2y+1}$ into the thermal or catalytic cracking unit; and (c) decomposing at least a portion of the ether to form (1) an olefin having a formula $C_xH_{2x}$ and/or $C_yH_{2y}$ and (2) an alcohol having a formula $C_xH_{2x+1}OH$ and/or $C_yH_{2y+1}OH$; wherein x and y independently range from about 1 to about 30.

In another embodiment, the invention relates to a method of making an olefin from a dialkyl ether further comprising (c) recovering at least a portion of the alcohol; (d) introducing at least a portion of the alcohol having the formula $C_xH_{2x+1}OH$ and/or $C_yH_{2y+1}OH$ into the thermal or catalytic cracking unit; and (e) decomposing at least a portion of the alcohol to form the olefin having the formula $C_xH_{2x}$ and/or $C_yH_{2y}$ and water.

In another embodiment, the invention relates to a method of making an olefin from a dialkyl ether wherein the hydrocarbon feedstock is one or more of crude oils, naphtha, vacuum gas oils (VGO), thermal oils, residual oils, cycle stocks, topped whole crudes, tar sand oils, shale oils, synthetic fuels, heavy hydrocarbon fractions derived from the destructive hydrogenation of coal, tar, pitches, asphalts, a gas-to-olefins derived feedstock and hydrotreated feedstocks derived from any of the foregoing items.

In another embodiment, the invention relates to a method of making an olefin from a dialkyl ether wherein the ether is introduced in a thermal or catalytic cracking unit at one or more points selected from (a) the feedstock feedline prior to addition of a dispersion steam stream, (b) a bottom section of the riser downstream of the hydrocarbon feed steam mixer and the regenerated catalyst return line, (c) a bottom section of a stripper, (d) a middle section of the stripper, (e) the top section of the stripper, (f) in a vapor line exiting the thermal or catalytic cracking unit, or (g) a fractionator.

In another embodiment, this invention relates to a method of reducing coking in a thermal or catalytic cracking unit comprising (a) introducing an ether, having a formula $C_xH_{2x+1}OC_yH_{2y+1}$, into the thermal or catalytic_cracking unit processing a hydrocarbon feedstock in an amount effective to reduce coke formation relative to processing the hydrocarbon feedstock in the absence of the ether, wherein x and y independently range from about 1 to about 30.

In another embodiment, this invention relates to a method of reducing coking in a FCC, a fluid coker, delayed coker or steam cracking unit, the method comprising (a) introducing an ether, having a formula $C_xH_{2x+1}OC_yH_{2y+1}$, into the unit processing a hydrocarbon feedstock in an amount effective to reduce coke formation relative to processing the hydrocarbon feedstock in the absence of the ether, wherein x and y independently range from about 1 to about 30.

Suitable thermal or catalytic cracking units for all embodiments include, but are not limited to, a FCC, a fluid coker, a delayed coker, and a steam cracking unit. For certain embodiments, a FCC is preferred.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
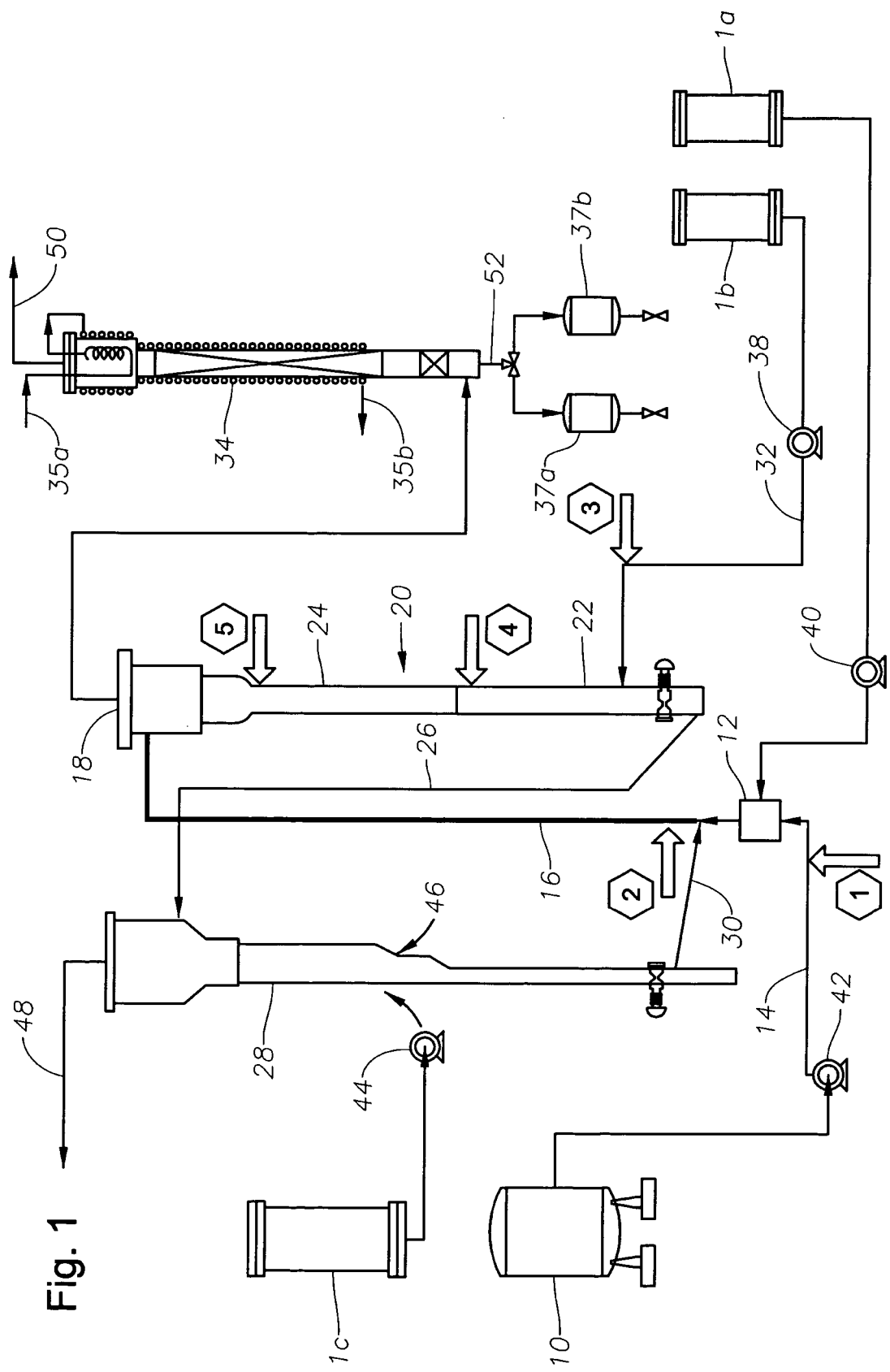
FIG. 1 is a schematic of a FCC pilot plant.

Applicants have developed a novel method of converting dialkyl ethers, considered low value by-products from certain processes used to make alcohols from olefins, to higher value products, i.e., alcohols and/or olefins. The alcohol represents additional product and the olefin can be converted to alcohols. Additionally, Applicants have developed an unexpected method of reducing coking in thermal and catalytic cracking units by injecting an ether into the hydrocarbon feedstock or various locations in a thermal or catalytic cracking unit.

Catalytic Cracking

Catalytic cracking is an established and widely used process in the petroleum refining industry for converting petroleum oils of relatively high boiling point to more valuable lower boiling products, including gasoline and middle distillates, such as kerosene, jet fuel and heating oil. The pre-eminent catalytic cracking process now in use is the Fluidized Catalytic Cracking (FCC) process in which a pre-heated feed is brought into contact with a hot cracking catalyst which is in the form of a fine powder, typically having a particle size of about 10-300 microns, usually about 60-70 microns, for the desired cracking reactions to take place. During the cracking, coke and hydrocarbonaceous material are deposited on the catalyst particles. This results in a loss of catalyst activity and selectivity. The coked catalyst particles, and associated hydrocarbon material, are subjected to a stripping process, usually with steam, to remove as much of the hydrocarbon material as technically and economically feasible. The stripped particles containing non-strippable coke are removed from the stripper and sent to a regenerator where the coked catalyst particles are regenerated by being contacted with air, or a mixture of air and oxygen, at an elevated temperature. This results in the combustion of the coke, which is a strongly exothermic reaction which, besides removing the coke, serves to heat the catalyst to the temperatures appropriate for the endothermic cracking reaction. The process is typically carried out in an integrated unit comprising the cracking reactor, the stripper, the regenerator, and the appropriate ancillary equipment. The catalyst is continuously circulated from the reactor or reaction zone, to the stripper and then to the regenerator and back to the reactor. The circulation rate is typically adjusted relative to the feed rate of the oil to maintain a heat balanced operation in which the heat produced in the regenerator is sufficient for maintaining the cracking reaction with the circulating regenerated catalyst being used as the heat transfer medium. Typical fluid catalytic cracking processes are described in the monograph Fluid Catalytic Cracking with Zeolite Catalysts, Venuto, P. B. and Habib, E. T., Marcel Dekker Inc. N.Y. 1979, which is incorporated herein by reference. As described in this monograph, catalysts that are conventionally used are based on zeolites, especially the large pore synthetic faujasites, zeolites X and Y.

Catalysts

The catalyst suitable of this invention includes all conventional catalysts typically used to catalytically "crack" hydrocarbon feeds. Typically, the catalytic cracking catalysts comprise a crystalline tetrahedral framework oxide component. This component is used to catalyze the breakdown of primary products from the catalytic cracking reaction into clean products such as naphtha for fuels and olefins for chemical feedstocks. Preferably, the crystalline tetrahedral framework oxide component is selected from the group consisting of zeolites, tectosilicates, tetrahedral aluminophosphates (AlPOs) and tetrahedral silicoaluminophosphates (SAPOs). More preferably, the crystalline framework oxide component is a zeolite.

Zeolites suitable for the present invention include, but are not limited to, both natural and synthetic zeolites with average pore diameters greater than about 0.7 nm. These zeolites are exemplified by gmelinite, chabazite, dachiardite, clinoptilolite, faujasite, heulandite, analcite, levynite, erionite, sodalite, cancrinite, nepheline, lazurite, scolecite, natrolite, offretite, mesolite, mordenite, brewsterite, and ferrierite. Included among the synthetic zeolites, but not limited to, are zeolites X, Y, A, L, ZK-4, ZK-5, B, E, F, H, J, M, Q, T, W, Z, alpha, beta, and omega, and USY zeolites. USY zeolites are preferred.

In general, aluminosilicate zeolites are suitable in this invention. However, the aluminum as well as the silicon component can be substituted by other framework components. For example, the aluminum portion can be replaced by boron, gallium, titanium or trivalent metal compositions that are heavier than aluminum. Germanium can be used to replace the silicon portion.

Feedstocks

Typical feeds to a catalytic cracker can generally be characterized as being a relatively high boiling oil or residuum, either on its own, or mixed with other fractions, also usually of a relatively high boiling point. The most common feeds are gas oils, that is, high boiling, non-residual oils, with an initial boiling point usually above about 230° C., more commonly above about 350° C., with end points of up to about 620° C. Typical gas oils include straight run (atmospheric) gas oil, vacuum gas oil (VGO), and coker gas oils. Other feeds include, but are not limited to, one or more of crude oils, naphtha, thermal oils, residual oils, cycle stocks, topped whole crudes, tar sand oil, shale oils, synthetic fuels, heavy hydrocarbon fractions derived from the destructive hydrogenation of coal, tar, pitches, asphalts, gas-to-olefins derived feedstock and hydrotreated feedstocks derived from any of the foregoing items Pilot Plant FCC Unit and Process With reference to FIG. 1, a hydrocarbon feedstream is pumped, by pump 42, from a hydrocarbon feed tank 10 to a feed-steam mixer 12 through a line 14 to form a feed-steam mixture. The steam, from water in tank 1a, fed into the mixer 12 via pump 40 is referred to as dispersion steam. The feed can be mixed with dispersion steam or an inert gas at such conditions that will form a highly atomized stream of a vaporous hydrocarbon-catalyst suspension, which undergoes reaction. This reacting catalyst suspension flows upward through a riser 16 into a stripper 20. The riser 16 is typically operated at a temperature of about 800-1200° F. (427-649° C.) and a pressure of about 0-100 psig (101-689.5 kPa).

In one embodiment, as shown in FIG. 1, the riser 16 is a FCC reactor vessel where the feed is contacted with a catalytic cracking catalyst. Water from tank 1a is converted to steam and fed as dispersion steam through pump 40 into riser 16. The feed-steam mixture is directed into the riser 16 where the hydrocarbon feed is converted to a cracked hydrocarbon product in this first stage, i.e., the riser 16, of the FCC unit. The vaporous hydrocarbon-catalyst suspension leaving the top of the riser 16 enters the upper portion 18 of a stripper column 20.

As the vaporous hydrocarbon-catalyst suspension leaves the top of the riser 16 and enters the upper section 18 of a stripper column 20, water from tank 1b is converted to stripping steam and conveyed by pump 38 into the bottom (or dense bed) section 22 of the stripper column 20 via steam line 32 and rises through the mid (or dilute phase) section 24 of the stripper column 20. The rising stripping steam carries the vaporous hydrocarbon out of the stripper column 20 toward a condenser 34. The condenser 34 has a coolant-in line 35a and a coolant-out line 35b. The condensed products are collected in accumulators 37a and 37b, via line 52. The non-condensed products exit the condenser 34 via line 50 for collection. The stripping steam essentially quenches the catalytic cracking reaction by separating the catalyst from the hydrocarbon vapor. The separated vapor comprises the cracked hydrocarbon product, and the separated catalyst contains a carbonaceous material (i.e., coke) as a result of the catalytic cracking reaction. The catalyst containing coke is removed from the stripper column 20 for regeneration.

The coked catalyst is typically continuously regenerated and recycled after the coke material has been removed. The coked catalyst is removed from stripper column 20 via line 26 and transferred to the upper section of the regeneration column 28. Steam from deionized water in tank 1c is provided by pump 44 and air, injected at point 46 on the catalyst regeneration column 28, are provided, typically countercurrent to the coked catalyst, to the regeneration column 28. As the coked catalyst moves down the regeneration column 28 the coke is combusted at a temperature of about 900-1400° F. (482-760° C.) and a pressure of about 0-100 psig (101-689.5 kPa). After the combustion step, the regenerated catalyst is recycled to the riser 16 from the regeneration column 28 via line 30. A flue gas exits the regeneration column 28 via line 48.

Figure 2:
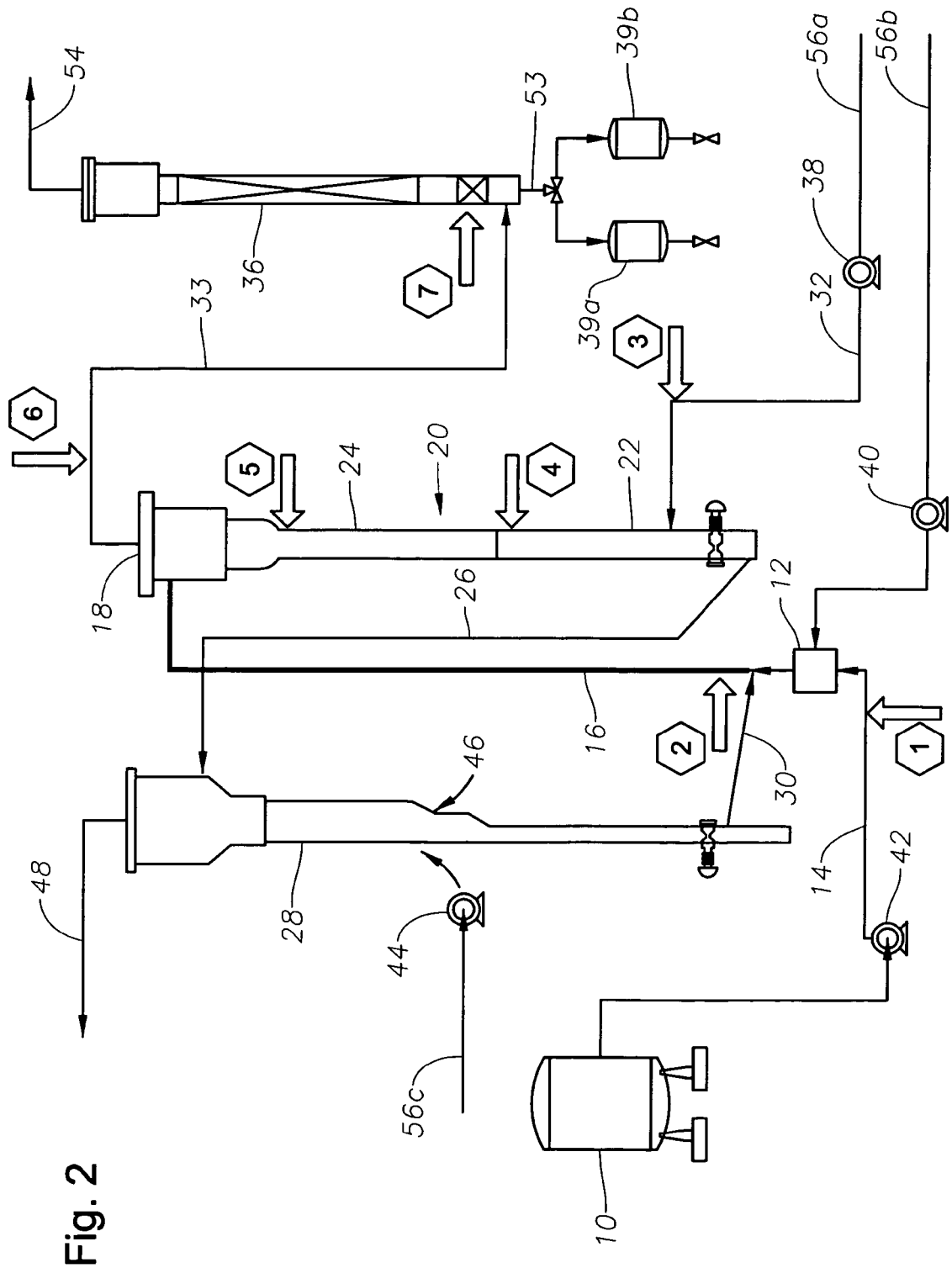
FIG. 2 is a schematic of a commercial FCC plant.

The commercial FCC unit, shown in FIG. 2, is similar to the pilot plant FCC unit, shown in FIG. 1, except that the commercial FCC unit uses steam from a carbon monoxide furnace, not shown, via lines 56a, 56b, and 56c. The commercial FCC unit has an accumulator 39a and 39b connected to the fractionator 36 by line 53. In the commercial FCC unit, vaporous hydrocarbon products are separated in a fractionator 36 from which clarified oil is removed from the bottom of the fractionator 36, heating oil is removed form a middle section of the fractionator 36 and liquefied petroleum gas and low pressure distillate are taken overhead via line 54 for further processing.

Ether Decomposition to Alcohol and/or Olefin

In one embodiment, this invention relates to a method of making an olefin from a dialkyl ether comprising (a) introducing at least about 1000 ppm by weight of a dialkyl ether having a formula $C_xH_{2x+1}OC_xH_{2x+1}$ into a thermal or catalytic cracking unit processing a hydrocarbon feedstock; and (b) decomposing at least a portion of the ether to form an olefin having a formula $C_xH_{2x}$ and an alcohol having a formula $C_xH_{2x+1}OH$, wherein x ranges from about 1 to about 30. In one embodiment, a preferred thermal or catalytic cracking unit is an FCC.

In another embodiment, this invention relates to a method of making an olefin from a dialkyl ether comprising (a) introducing at least one ether having a formula $C_xH_{2x+1}OC_yH_{2y+1}$ into a thermal or catalytic cracking unit processing a hydrocarbon feedstock; and (b) decomposing at least a portion of the ether to form (1) an olefin having a formula $C_xH_{2x}$ and/or $C_yC_{2y}$, and (2) an alcohol having a formula $C_xH_{2x+1}OH$ and/or $C_yH_{2y+1}OH$ wherein x and y independently range from about 1 to about 30. In one embodiment, a preferred thermal or catalytic cracking unit is an FCC.

In one embodiment, the olefins are prepared from dialkyl ethers having a formula $C_xH_{2x+1}OC_xH_{2x+1}$, wherein x ranges from about 1 to about 30, preferably from about 1 to about 8, more preferably from about 1 to 4. In one embodiment, the olefins are prepared from a dialkyl ether having a formula $C_xH_{2x+1}OC_yH_{2y+1}$, wherein x and y independently range from about 1 to about 30, preferably from about 1 to about 8, more preferably from about 1 to 4. The ethers include, but are not limited to, di-isopropyl ether (IPE), methyl tert-butyl ether (MTBE) and di-secondary butyl ether (SBE). In one embodiment, the ether further comprises an alcohol having the formula $C_xH_{2x+1}OH$ and/or $C_yH_{2y+1}OH$, wherein x and y independently range from about 1 to about 30, preferably from about 1 to about 8, more preferably from about 1 to 4.

In one embodiment, the ether comprises a mixture of two or more ethers. In another embodiment, the ether further comprises a non-ether compound, for example, either IPE having a purity of about 91 weight % or SBE having a purity of about 55 weight %, with the remainder being a mixture of $C_8$ olefins and other oxygenates.

In one embodiment, the method comprises introducing from about 0.1 weight % to about 15 weight % of the ether having a formula $C_xH_{2x+1}OC_xH_{2x+1}$ or $C_xH_{2x+1}OC_yH_{2y+1}$ into the thermal or catalytic cracking unit, preferably a FCC unit, preferably from about 0.5 weight % to about 15 weight % of the ether, and more preferably from about 1 weight % to about 15 weight % of the ether based on the total weight of the feedstock and the ether. In another embodiment, the method comprises introducing at least about 0.1 weight % of the ether, preferably at least about 0.5 weight % of the ether, and more preferably at least about 1 weight % of the ether based on the total weight of the feedstock and the ether.

One embodiment of the method of making olefins further comprises recovering at least a portion of the alcohol formed from the ether, introducing at least a portion of the alcohol into the thermal or catalytic cracking unit, and decomposing at least a portion of the alcohol to form the corresponding olefin. One embodiment further comprises recovering at least about 50 weight % of the alcohol formed from the ether, preferably at least about 90 weight % of the alcohol formed from the ether, more preferably at least about 95 weight % of the alcohol formed from the ether, and yet more preferably at least about 99 weight % of the alcohol formed from the ether. One embodiment comprises introducing at least about 50 weight % of the recovered alcohol into the thermal or catalytic cracking unit, preferably at least about 90 weight % of the recovered alcohol, more preferably at least about 95 weight % of the recovered alcohol, and yet more preferably at least about 99 weight % of the recovered alcohol. One embodiment comprises decomposing at least about 50 weight % of the recovered alcohol to form the corresponding olefin, preferably at least about 90 weight % of the recovered alcohol, more preferably at least about 95 weight % of the recovered alcohol, and yet more preferably at least about 99 weight % of the recovered alcohol.

In various embodiments of the present invention the dialkyl ethers are independently introduced into the thermal or catalytic cracking unit at one or more points selected from (a) the feedstock feedline prior to addition of a dispersion steam stream, (b) a bottom section of the riser downstream of the hydrocarbon feed steam mixer and the regenerated catalyst return line, (c) a bottom section of a stripper, (d) a middle section of the stripper, (e) the top section of the stripper, (f) in a vapor line exiting the stripper column (6), or (g) a fractionator (7). The location of the ether injection determines the residence time of the ether in the thermal or catalytic cracking unit. As shown in Table 1, the residence time ranges from about 3 seconds to about 96 seconds, as exemplified for a FCC pilot plant. As Table 2 further shows, the ether decomposition for IPE/SBE blends was complete, except for injection in the upper section of the dilute phase 24 of the stripper column 20, which still provided 99 weight % conversion. In one embodiment, at least about 50 weight % of the ether is converted into the corresponding alcohol and/or olefin, more preferably at least about 90 weight % of the ether is converted into the corresponding alcohol and/or olefin, and yet more preferably at least about 99 weight % of the ether is converted into the corresponding alcohol and/or olefin.

The catalyst to hydrocarbon feed ratio can affect the residence time of the feed in the thermal or catalytic cracking unit. In a FCC unit operating at greater than about 900° F. (482° C.) the catalyst to hydrocarbon feed ratio ranges from about 3 to about 9, preferably from about 5 to about 7 based on the total weight of the catalyst and hydrocarbon feed.

In all of the foregoing embodiments the ether may be co-injected into the thermal or catalytic cracker with a carrier gas. The carrier gas includes, but is not limited to, steam, nitrogen and light hydrocarbons. Light hydrocarbons include, but are not limited to, methane and ethane.

Ether Decomposition and Coking

In another embodiment, this invention relates to a method of reducing coking in a thermal or catalytic cracking unit comprising introducing an ether, having a formula $C_xH_{2x+1}OC_yH_{2y+1}$, into the thermal or catalytic cracking unit processing a hydrocarbon feedstock in an amount effective to reduce coke formation relative to processing the hydrocarbon feedstock in the absence of the ether, wherein x and y independently range from about 1 to about 30. The embodiments disclosed above for preparing olefins from ethers decomposition in a thermal cracker, and specifically a FCC, may be used in the process of reducing coking, with the exception that the minimum amount of ether used in the process to reduce coking must be an amount effective to reduce coking.

In one embodiment, the ethers as previously described above may also be introduced into a thermal or catalytic cracking unit, including but not limited to a FCC unit, a delayed coker unit, a fluidized coker unit and a steam cracking unit, to reduce coking. Table 1 shows that the coke yield ranged from a negative yield to about 17 weight % based on the ether. The negative coke yield indicates that the coke formation was less in the process having an ether introduced into the FCC unit than the coke yield for the same hydrocarbon cracking process without the ether. The reduced coking may allow the catalyst to have a higher activity or permit faster regeneration when less coke must be removed from the catalyst. The reduced coke formation may affect the heat balance for the FCC unit since the combustion of the coke in the regeneration column is exothermic and provides heat to the riser when the hot, regenerated catalyst is recycled to the riser. However, a lower coke yield also provides a higher yield of other useful products. Furthermore, some FCC units produce too much coke and need to remove heat from the regeneration of the catalyst to satisfy the heat balance, which means that a reduction in coking is desirable in some systems.

In one embodiment the incremental coke yield from ether decomposition is less than or equal to about 17 weight % based on the ether. Alternatively the incremental coke yield is less than or equal to about 5 weight % based on the ether. Alternatively, the incremental coke yield is about 0 weight % based on the ether. The incremental coke yield, when referring to a negative yield, is the amount of coke attributable to or inhibited by the decomposition of the ether and is determined by taking the difference of the coke yields of, for example, an FCC process run without the ether and then the same FCC process run with the ether injected into the process. A positive incremental coke yield indicates that the coke yield increases in the presence of ether in the process. A negative incremental coke yield indicates that the coke yield is reduced in the presence of ether in the process.

In a similar manner, in one embodiment the introduction of an ether into an FCC unit caused a negative yield of the 430+° F. fraction of the cracked hydrocarbon products, as shown in Table 1. As with the negative coke yield, the negative 430+° F. yield indicates that less material having a boiling point equal to or greater than 430+° F. is made in an FCC unit, having an ether injected into the FCC unit, relative to the same process absent the ether.

The following non-limiting items are intended to be included within the scope to the present invention.

Item 1. A method of making an olefin from a dialkyl ether, the method comprising:
 (a) introducing an ether having a formula $C_xH_{2x+1}OC_yH_{2y+1}$ into a thermal or catalytic unit processing a hydrocarbon feedstock; and
 (b) decomposing at least a portion of the ether to form (1) an olefin having a formula $C_xH_{2x}$ and/or $C_yH_{2y}$, and (2) an alcohol having a formula $C_xH_{2x+1}OH$ and/or $C_yH_{2y+1}OH$;
 wherein x and y independently range from about 1 to about 30.

Item 2. The method according to item 1, wherein x and y have the same value.

Item 3. The method according to any of the preceding items, wherein the ether is introduced in an amount effective to reduce coke formation relative to processing the hydrocarbon feedstock in the absence of the ether.

Item 4. The method according to any of the preceding items, wherein at least about 1000 ppm by weight of the ether is introduced into the thermal or catalytic unit.

Item 5. The method according to any of the preceding items, further comprising:

(c) recovering at least a portion of the alcohol;

(d) introducing at least a portion of the alcohol into the thermal or catalytic cracking unit; and (e) decomposing at least a portion of the alcohol to form the olefin.

Item 6. The method according to any of the preceding items, wherein the thermal or catalytic cracking unit is selected from a fluidized catalytic cracker, a delayed coker, a fluid coker or a steam cracking unit.

Item 7. The method according to any of the preceding items, wherein the feedstock is one or more of crude oils, naphtha, vacuum gas oils, thermal oils, residual oils, cycle stocks, topped whole crudes, tar sand oil, shale oils, synthetic fuels, heavy hydrocarbon fractions derived from the destructive hydrogenation of coal, tar, pitches, asphalts, a gas-to-olefins derived feedstock and hydrotreated feedstocks derived from any of the foregoing items.

Item 8. The method according to any of the preceding items, wherein the thermal or catalytic cracking unit comprises a stripper bed operating at a temperature ranging from at least about 480° C. to about 650° C.

Item 9. The method according to any of the preceding items, wherein the ether and the alcohol are each independently introduced at one or more points in the thermal or catalytic cracking unit selected from (a) the feedstock feedline prior to addition of a dispersion steam stream, (b) a bottom section of the riser downstream of the hydrocarbon feed steam mixer and the regenerated catalyst return line, (c) a bottom section of a stripper, (d) a middle section of the stripper, (e) the top section of the stripper, (f) in a vapor line exiting the stripper, or (g) a fractionator.

Item 10. The method according to any of the preceding items, wherein the ether comprises from about 0.1 weight % to about 15 weight % of the total weight of the feedstock and the ether.

Item 11. The method according to any of the preceding items, wherein the ether comprises from about 0.5 weight % to about 5 weight % of the total weight of the feedstock and the ether.

Item 12. The method according to any of the preceding items, wherein the ether comprises from about 1 weight % to about 5 weight % of the total weight of the feedstock and the ether.

Item 13. The method according to any of the preceding items, wherein the ether comprises from at least about 1 weight % of the total weight of the feedstock and the ether.

Item 14. The method according to any of the preceding items, wherein at least about 50 weight % of the ether is converted to the olefin and/or the alcohol.

Item 15. The method according to any of the preceding items, wherein at least about 90 weight % of the ether is converted to the olefin and/or the alcohol.

Item 16. The method according to any of the preceding items, wherein at least about 99 weight % of the ether is converted to the olefin and/or the alcohol.

Item 17. The method according to any of the preceding items, wherein a liquefied petroleum gas yield ranges from about 10 weight % to about 82 weight %.

Item 18. The method according to any of the preceding items, wherein the liquefied petroleum gas comprises $C_3$ and $C_4$ olefins ranging from about 35 weight % to about 91 weight % of the total weight of the liquefied petroleum gas.

Item 19. The method according to any of the preceding items further comprising converting the feedstock to products comprising coke, wherein the incremental coke yield is less than about 17 weight %.

Item 20. The method according to any of the preceding items, wherein x and y independently range from about 1 to 10.

Item 21. The method according to any of the preceding items, wherein x and y independently range from about 1 to 4.

Item 22. The method according to any of the preceding items 1 through 20, wherein x and y independently range from about 3 to 8.

Item 23. The method according to any of the preceding items, wherein x and y independently range from about 3 to 4.

Item 24. The method according to any of the preceding items, wherein the ether and the alcohol are each independently introduced at one or more points in the thermal or catalytic cracking unit selected from (a) the feedstock feedline prior to addition of a dispersion steam stream, (b) a bottom section of the riser downstream of the hydrocarbon feed steam mixer and the regenerated catalyst return line, (c) a bottom section of a stripper, (d) a middle section of the stripper, (e) the top section of the stripper, (f) in a vapor line exiting the stripper, or (g) a fractionator.

Item 25. The method according to any of the preceding items, wherein the ether is atomized.

Item 26. The method according to any of the preceding items, further comprising injecting a carrier gas with the ether, wherein the carrier gas comprises steam, nitrogen, and light hydrocarbon gases.

Although the foregoing embodiments frequently exemplify the methods according to the present invention in terms of a FCC unit, this is for purposes of illustration only. Thermal or catalytic cracking units including, but are not limited to, a delayed coker, a fluid coker or a steam cracker also may be suitably employed in all of the foregoing embodiments.

EXAMPLES

Example 1

General Procedure

The pilot plant unit was started up with a vacuum gas oil (VGO) hydrocarbon feed and operated until the desired operating conditions were reached. While the pilot plant was operating at the desired process conditions a first material balance based on the VGO feed was obtained. Then the ether feed was injected, at the points indicated in Table 1. The ether feed was vaporized in the feed line at about 320° F. (160° C.) before reaching the designated injection location. Once the unit was lined-out a second material balance was obtained.

The ether feed was approximately 5 weight % of the total feed. The ether feed was a blend of about two parts of isopropyl ether (IPE) to one part of secondary butyl ether (SBE) by volume. The IPE purity was 91% and the SBE purity was 55%, with the remainder being primarily $C_8$ olefins. Purity is measured by GC and GCMS analyses.

TABLE 1

Pilot Plant Results

| Injection Location | Lpg Yield, Wt % of Ether | % C3/C4 Olefins In Lpg | Coke Yield, Wt % of Ether | Yield of 430 F+, Wt % of Ether | % Ether Decomposition | Residence Time (Seconds) | Catalyst To Oil Ratio |
|---|---|---|---|---|---|---|---|
| 1 | 71 | 86 | −5.3 | −11.7 | 100 | 3 | 5.9 |
| 1 | 71 | 83 | −2.5 | −2.1 | 100 | 3 | 7.2 |
| 2 | 41 | 100 | −4.8 | 54 | 100 | 3 | 6.1 |
| 2 | 82 | 88 | 1.6 | −5.6 | 100 | 3 | 7.1 |
| 3 | 29 | 35 | 17.5 | 8.5 | 100 | 96 | 6 |
| 4 | 55 | 59 | 4.7 | 3.0 | 100 | 92 | 6 |
| 5 | 79 | 91 | −6.9 | 37.5 | 99 | 76 | 5.6 |

Example 2

The tests were run in a commercial FCC. Three injection points were tested. The IPE/SBE was blended in a 2:1 ratio by volume. The IPE/SBE blend was fed to the FCC unit at 1 weight % based on the weight of the hydrocarbon feed which was VGO.

TABLE 2

Plant FCC Unit Results

| | Ether Injection Location | Equivalent Location In FIG. 1 | Wt % Ether Decomposition | Total Oxygen In LPD | Coking |
|---|---|---|---|---|---|
| 1 | Into stripper with steam | 3 | Complete | | No change |
| 2 | FCC effluent to fractionator | line 33 near fractionator 36 | 83–90% | LPD 139 wppm 163 wppm | No change |
| 3 | FCC effluent to fractionator feed | 33 at exit of stripper 20 to line 33 | 83–90% | LPD 139 wppm 163 wppm | No change |

LPD—low pressure distillate (naphtha)

All documents described herein are incorporated by reference herein, including any priority documents and/or testing procedures. As is apparent from the foregoing general description and the specific embodiments, while forms of the invention have been illustrated and described, various modifications can be made without departing from the spirit and scope of the invention. Accordingly, it is not intended that the invention be limited thereby.

The invention claimed is:

1. A method of making an olefin from a dialkyl ether, the method comprising:
    (a) independently introducing an ether having a formula $C_xH_{2x+1}OC_yH_{2y+1}$ into a thermal or catalytic cracking unit selected from the group consisting of a FCC, a delayed coker, a fluid coker, or a steam cracking unit, said thermal or catalytic unit processing a hydrocarbon feedstock selected from the group consisting of crude oils, naphtha, vacuum gas oils, thermal oils, residual oils, cycle stocks, topped whole crudes, tar sand oil, shale oils, synthetic fuels, heavy hydrocarbon fractions derived from the destructive hydrogenation of coal, tar, pitches, asphalts, a gas-to-olefins derived feedstock, hydrotreated feedstocks derived therefrom, and mixtures thereof; and
    (b) decomposing at least a portion of said ether to form (1) an olefin having a formula $C_yH_{2x}$ and/or $C_yH_{2y}$, and (2) an alcohol having a formula $C_xH_{2x+1}OH$ and/or $C_yH_{2y+1}OH$;
    (c) recovering at least a portion of the alcohol;
    (d) introducing at least a portion of the alcohol into the thermal or catalytic cracking unit;
    (e) decomposing at least a portion of the alcohol to form the olefin;
    wherein the ether comprises from at least about 1 weight % to about 5 weight % of the total weight of the feedstock and the ether;
    wherein x and y independently range from about 1 to 10; and
    whereby said ether reduces coke formation relative to processing said hydrocarbon feedstock in the absence of said ether.

2. The method according to claim 1, wherein a liquefied petroleum gas yield ranges from about 10 weight % to about 82 weight %.

3. The method according to claim 2, wherein the liquefied petroleum gas comprises $C_3$ and $C_4$ olefins ranging from about 35 weight % to about 91 weight % of the total weight of the liquefied petroleum gas.

4. The method according to claim 1, wherein x and y independently range from about 1 to 10.

5. The method according to claim 1, wherein the ether and the alcohol are each independently introduced at one or more points in the thermal or catalytic cracking unit selected from (a) the feedstock feedline prior to addition of a dispersion steam stream, (b) a bottom section of the riser downstream of the hydrocarbon feed steam mixer and the regenerated catalyst return line, (c) a bottom section of a stripper, (d) a middle section of the stripper, (e) the top section of the stripper, (f) in a vapor line exiting the stripper, or (g) a fractionator.

6. The method according to claim 1, wherein the thermal or catalytic cracking unit comprises a stripper bed operating at a temperature ranging from at least about 480° C. to about 650° C.

* * * * *

UNITED STATES PATENT AND TRADEMARK OFFICE
CERTIFICATE OF CORRECTION

| | | |
|---|---|---|
| PATENT NO. | : 7,655,826 B2 | Page 1 of 1 |
| APPLICATION NO. | : 11/104315 | |
| DATED | : February 2, 2010 | |
| INVENTOR(S) | : Yarbrough et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1290 days.

Signed and Sealed this

Twenty-third Day of November, 2010

David J. Kappos
*Director of the United States Patent and Trademark Office*